US009791357B2

(12) United States Patent
Myers et al.

(10) Patent No.: US 9,791,357 B2
(45) Date of Patent: Oct. 17, 2017

(54) OVERLOAD INDICATOR FOR HOIST

(71) Applicants: Steven Myers, Buffalo Valley, TN (US); Charles Weber, Onalaska, WI (US)

(72) Inventors: Steven Myers, Buffalo Valley, TN (US); Charles Weber, Onalaska, WI (US)

(73) Assignee: JPW Industries Inc., La Vergne, TN (US)

( * ) Notice: Subject to any disclaimer, the term of this patent is extended or adjusted under 35 U.S.C. 154(b) by 117 days.

(21) Appl. No.: 14/811,155

(22) Filed: Jul. 28, 2015

(65) Prior Publication Data

US 2017/0030813 A1   Feb. 2, 2017

(51) Int. Cl.
| | |
|---|---|
| *B66C 15/06* | (2006.01) |
| *G01L 5/04* | (2006.01) |
| *G01N 3/08* | (2006.01) |
| *B66D 1/54* | (2006.01) |

(52) U.S. Cl.
CPC .............. *G01N 3/08* (2013.01); *B66C 15/06* (2013.01); *B66D 1/54* (2013.01); *G01L 5/047* (2013.01)

(58) Field of Classification Search
CPC .. B66C 1/12; B66C 1/125; B66C 1/14; B66C 15/06; G01L 1/06; G01L 5/0071; G01L 5/04; G01L 5/047; G01L 5/06; G01N 3/08
USPC ........................................ 116/212; 73/862.53
See application file for complete search history.

(56) References Cited

U.S. PATENT DOCUMENTS

| | | | |
|---|---|---|---|
| 3,077,178 A | 2/1963 | Gordon | |
| 3,885,428 A * | 5/1975 | Dalferth | G01L 5/047 116/DIG. 34 |
| 3,908,452 A * | 9/1975 | Rieger | G01L 5/101 73/862.392 |
| 4,578,941 A | 4/1986 | Butterfield | |
| 5,655,476 A * | 8/1997 | Wolter | B66C 1/125 116/212 |
| 6,488,434 B1 | 12/2002 | Graeff | |
| 7,607,401 B2 | 10/2009 | McCauley | |
| 7,634,949 B2 | 12/2009 | Lodge et al. | |
| 7,938,468 B2 * | 5/2011 | Mueller | B66C 1/18 294/74 |

FOREIGN PATENT DOCUMENTS

| | | | | |
|---|---|---|---|---|
| AT | 378264 B | * | 7/1985 | ............. G01L 5/047 |
| DE | 2728698 A1 | | 1/1979 | |
| DE | 2755428 A1 | * | 6/1979 | ............... G01L 1/06 |
| EP | 0003685 A2 | | 8/1979 | |
| GB | 1426965 A | * | 3/1976 | |

(Continued)

*Primary Examiner* — Richard A Smith
(74) *Attorney, Agent, or Firm* — Schiff Hardin LLP (57) ABSTRACT

An overload indicator for a hoist includes first and second blocks that connect to the lifting medium (a chain for a chain hoist) at spaced locations. The first and second blocks are held at a spacing by indicator bands so that the lifting medium is slack between the blocks. The indicator bands have weakened portions to deform, stretch or break when subject to a load over a threshold, such as over a lifting capacity of the hoist. Covers are provided over the indicator bands that are closely spaced to define an indicator gap. If the indicator bands stretch, the indicator gap increases to indicate an overload condition.

17 Claims, 9 Drawing Sheets

(56) References Cited

FOREIGN PATENT DOCUMENTS

| | | | | | |
|---|---|---|---|---|---|
| GB | 1434230 | A | * | 5/1976 | ............. G01L 5/047 |
| GB | 1452705 | A | | 10/1976 | |
| GB | 2043922 | A | | 10/1980 | |
| GB | 2183350 | A | * | 6/1987 | ............. B66C 1/125 |
| JP | 06074875 | A | * | 3/1994 | ............... G01L 1/06 |

* cited by examiner

OVERLOAD INDICATOR FOR HOIST

BACKGROUND OF THE INVENTION

Field of the Invention

The present invention relates generally to an overload indicator for a hoist, and more particularly to an overload indicator for use with a chain hoist.

Description of the Related Art

A hoist may be used to lift or lower objects or to exert a tension force in a desired direction. A hoist may be manually operated, electrically operated, pneumatically operated, or powered by some other power source. A hoist typically uses a chain, fiber rope or wire rope as the lifting medium. Hoists are used in a wide variety of industries and situations.

Many hoists are assigned a rated capacity as the maximum load that should he lifted by the hoist. Even though hoists may be designed with a safety margin above the rated capacity, a hoist can be damaged by lifting loads beyond its rated capacity, particularly if the load is several times the rated capacity of the hoist. The damage caused to the hoist by lifting too heavy of a load may not be apparent to the user or another person, such as a tool crib manager. Subsequent use of the damaged hoist may result in failure of the hoist,

SUMMARY OF THE INVENTION

The present invention provides an overload indicator for a hoist. The overload indicator is attached to the chain or other lifting media that extends between the hoist and the load so that the overload indicator is in line with the chain. The overload indicator includes two brackets or block portions connected to the chain or other lifting media at locations spaced from one another, The brackets or block portions are connected to one another by a band, and preferably two bands, that hold a length of the chain or other lifting media slack between the brackets or block portions, so that the load being applied to the chain, and thus to the hoist, is applied to the bands. The bands are of a material and configuration intended to stretch, break or otherwise deform when a load above a predetermined threshold is applied. During or after use of the hoist, the bands may be examined for stretching, breakage, or deformation to determine whether an overload has been applied to the hoist, In certain embodiments, the overload indicator includes covers that extend over the bands. The covers are mounted to the brackets or block portions and extend partly or completely over the bands. The covers are mounted to provide an indicator gap between portions of the covers. The indicator gap may be at a first gap length when the indicator bands are in their un-stretched and un-deformed state. For example, the portions of the cover may abut or nearly abut one another. If the overload indicator is subjected to a load greater than the threshold, one or both of the indicator bands deforms or stretches, resulting in the portions of the cover moving apart and increasing the length of the indicator gap. The increase in the indicator gap distance may be easier for a user to detect than a stretching or deforming of the indicator bands alone.

A gap distance greater than the first gap distance may indicate that an overload has been applied to the overload indicator, and thus to the hoist. The user may check the indicator gap distance to determine if one or both bands has stretched or deformed.

In certain embodiments, the covers may be configured to protect the bands from damage. The undamaged bands may retain the desired threshold, whereas a damaged band may deform more readily under less than threshold loads. Damage to the bands from handling may be misinterpreted as damage as a result of an overload condition. The covers may shield a user or other person from injury due to breakage of a band.

DETAILED DESCRIPTION OF THE PREFERRED EMBODIMENTS

Figures 1, 2:
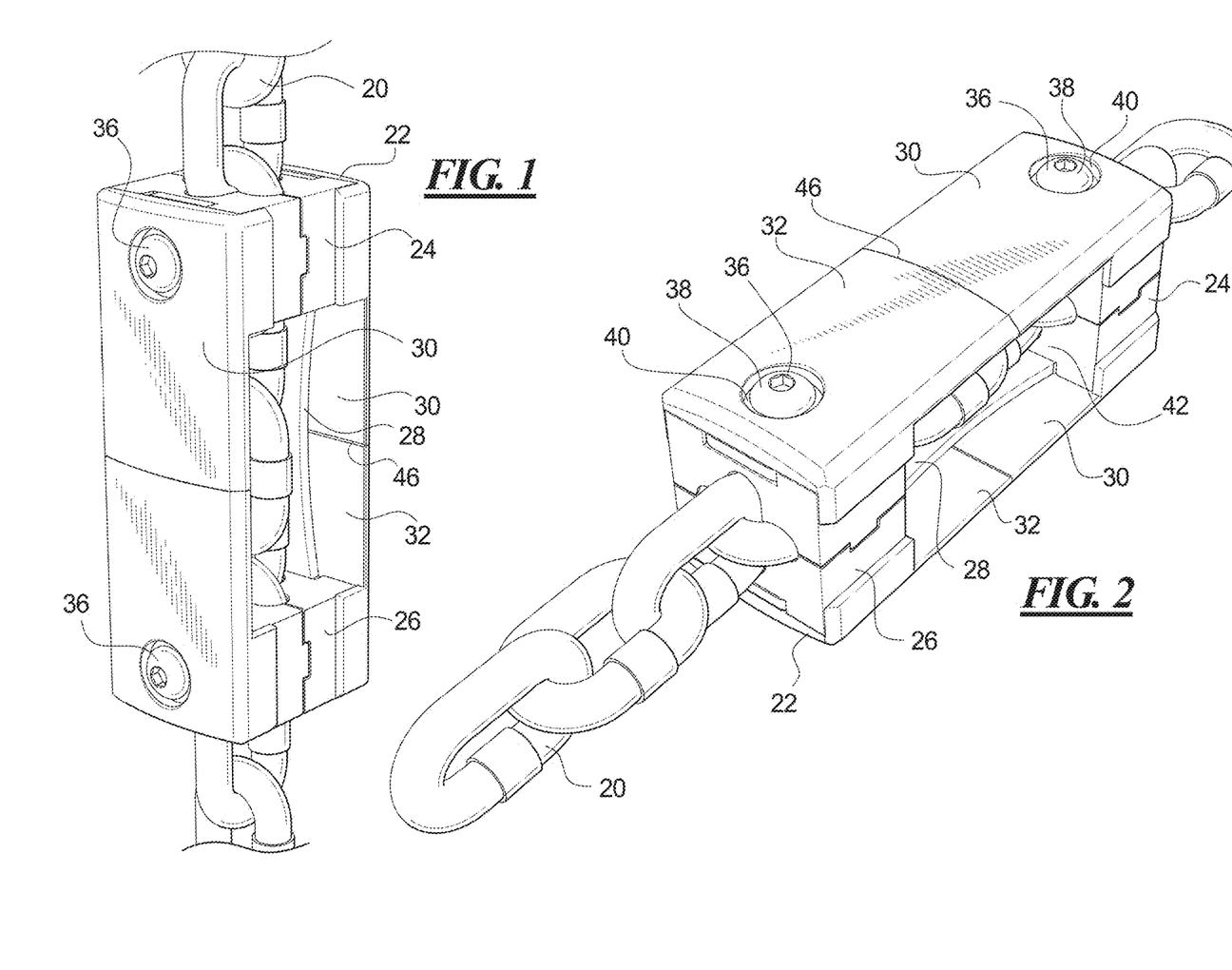
FIG. 1 is a perspective view of an overload indicator for use with a hoist, the overload indicator being mounted on a chain.
FIG. 2 is a side perspective view showing components of the overload indicator.
Figure 13:
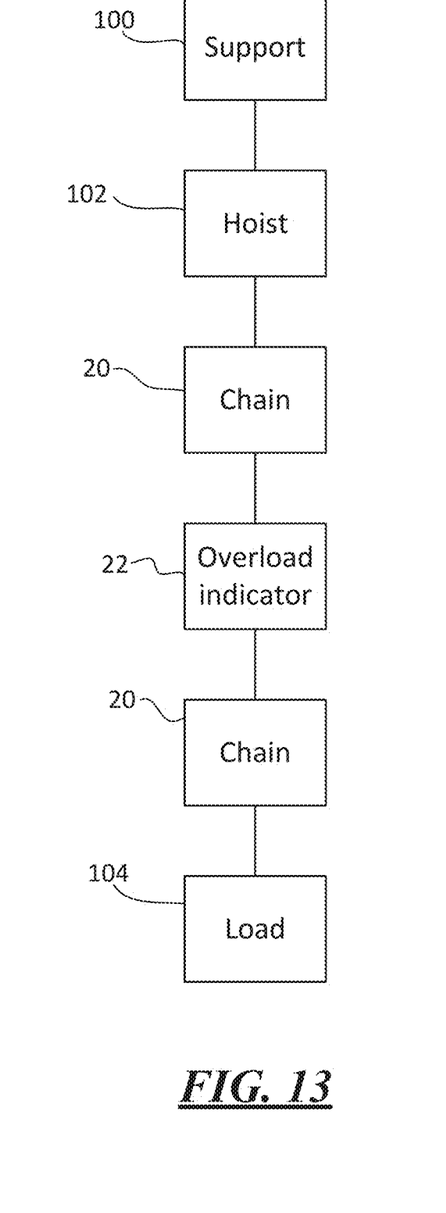
FIG. 13 is a functional block diagram showing the arrangement of components from a support for the hoist to the load.

In FIG. 1, a chain 20 is provided as a lifting medium for a hoist. As can be seen in FIG. 13, the chain extends between the hoist and the load. A hook is typically provided at the free end of the chain to which the load is attached, although other means of connecting the load may be provided. The entire load that is lifted by the hoist is transmitted through the chain. The chain is but one example of a lifting medium. Other lifting mediums are possible as well, including wire cable, a fiber rope, or other lifting medium.

An overload indicator 22 is connected along a length of the chain 20. For example, the overload indicator 22 may be connected between the hoist and the load. It is also possible that the overload indicator may be connected between the hoist and a support from which the hoist is suspended, or at another location that transmits the force of the load. The overload indicator 22 includes a first block portion 24 connected at a first location along the chain 20 and a second block portion 26 connected at a second location along the chain. The first and second locations are spaced from one another. An indicator band 28 is connected between the blocks 24 and 26. The indicator band 28 is of a length to hold the chain 20 or other lifting medium slack between the blocks 24 and 26. By maintaining the lifting medium slack between the blocks 24 and 26, the force of the load is carried by the indicator band 28.

In the illustrated embodiment, covers 30 and 32 are connected to the blocks 24 and 26. The covers 30 and 32 extend over at least a portion of the indicator band 28. The covers 30 and 32 are connected by bolts 36 and nuts. Other connectors are possible instead.

FIG. 2 shows the overload indicator 22 in an end view. The covers 30 and 32 are held in place by bolts 36. Although any type of bolt or other connector may be provided, the illustrated embodiment includes bolts 36 that have a hexagonal recess in the bolt head 38 to receive a hex key or Allen wrench. Each of the heads 38 are in a recess 40 in the covers 30 and 32. The bolts 36 are provided at the first and second block portions 24 and 26. A gap 42 is provided between the first and second block portions 24 and 26. Covers 30 and 32 are also visible on the opposite side of the overload indicator 22. The covers 30 and 32 on both sides extend across the gap 42 between the block portions 24 and 26.

Figure 3:
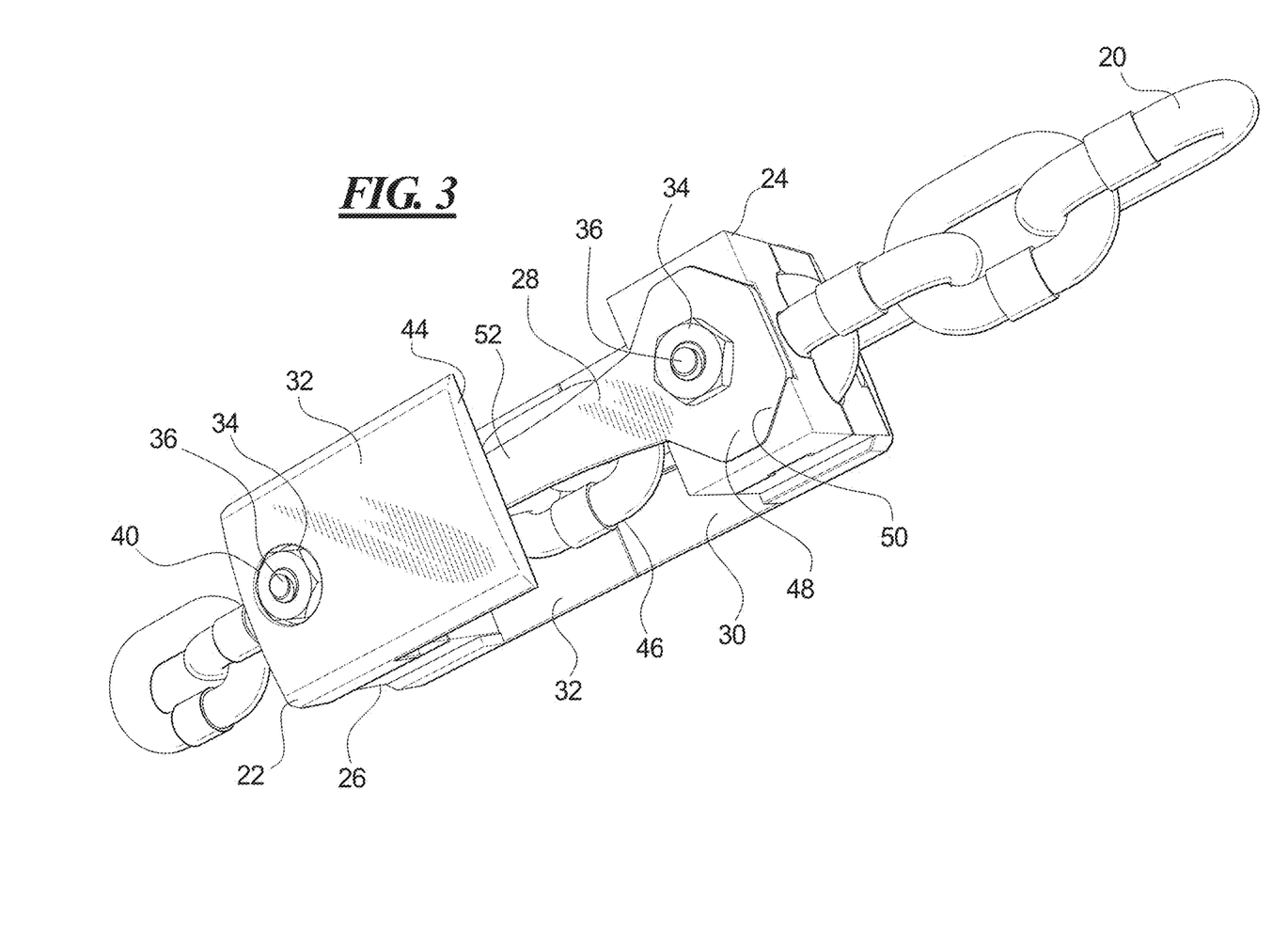
FIG. 3 is a side perspective view of the overload indicator with a first cover portion removed to reveal a portion of an indicator band and link mounting block.

FIG. 3 shows the overload indicator with one of the covers 30 removed from one side. The other cover 32 on that side remains in place and the covers 30 and 32 on the other side are in place. The covers 30 and 32 include recesses 40 into which threaded nuts 34 are received when the nuts 34 are threaded on to the bolts 36. To remove the cover 30, the nut 34 is removed from the bolt 36. The nut 34 has been reconnected to the bolt in this view. With the cover 30 removed, an end surface 44 of the cover 32 is apparent. The end 44 ordinarily is closely adjacent or abutting a similar end of the cover 30. The closely adjacent or abutting ends 44 of the covers 30 and 32 form an indicator gap 46. The indicator gap 46 may be closed or nearly closed or at some other spacing. In the example, the indicator gap 46 is closed when the overload indicator has not been subjected to an overload condition. The gap 46 opens after an overload condition, as will be described.

With the cover 30 removed, a portion of the indicator band 28 is visible. The indicator band 28 includes a shaped portion 48 through which the bolt 36 extends. The shaped portion 48 is positioned in a shaped recess 50 in the block portion 24. A tapered portion 52 extends from the shaped portion 48. The tapered portion 52 provides a weakened area of the indicator band 28. The shaped recess 50 in the block portion 24 is configured to correspond in shaped to the shaped portion 48 so that the shaped portion 48 fits into the recess 50 with little or no play. Little or no rotational movement may be possible between the shaped portion 48 and the shaped recess 50. In the illustrated example, the shaped portion 48 and shaped recess 50 are generally hexagonally shaped with flat edge portions at angles to one another that restrict rotation of the indicator band 28 within the block 24.

Figure 4:
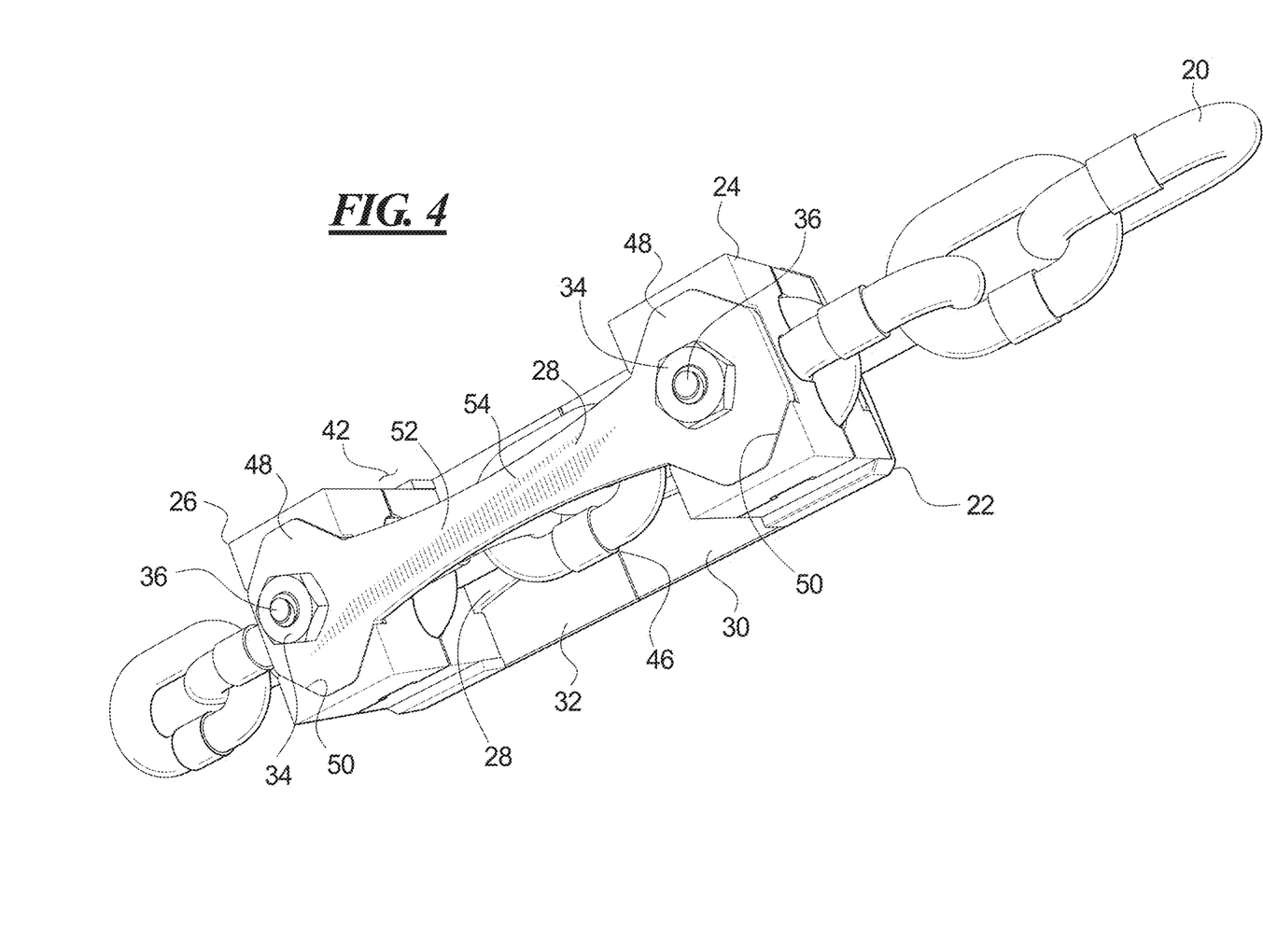
FIG. 4 is a side perspective view of the overload indicator with first and second cover portions removed to reveal the entire indicator band.

Turning to FIG. 4, both covers 30 and 32 have been removed from one side of the overload indicator 22, although the covers 30 and 32 remain in place on the other side. The indicator band 28 has a shaped portion 48 at both ends. The shaped portions 48 fit into corresponding recesses 50 in the first and second block portion 24 and 26. The tapered portion 52 is shaped to narrow along its length to provide a weakened portion 54. In weakened portion 54 is generally at a middle of the indicator band 28 although the weakened portion 54 may be at any position along the band 28. The weakened portion 54 may deform, stretch or even break when subject to a tension force in excess of a threshold.

The material, shape and dimensions of the indicator band 28 and particularly the tapered portion 52 are selected to provide a desired tension force threshold. The bands may be of steel. Examples may include a stretching or deformation threshold got hoists having a rated lifting capacity of ⅛ ton, ¼ ton, ½ ton, one ton, two tons, three tons, five tons, or ten tons. The thresholds may correspond to the rated capacity of the hoist. For example, the threshold for deforming or stretching of the indicator band may equal the rated capacity of the hoist, or may exceed the rated capacity by a predetermined percent. For example, the deformation threshold may be set to 1.5 times the rated capacity of the hoist or some other value. Other thresholds are of course possible.

Figures 5, 10:
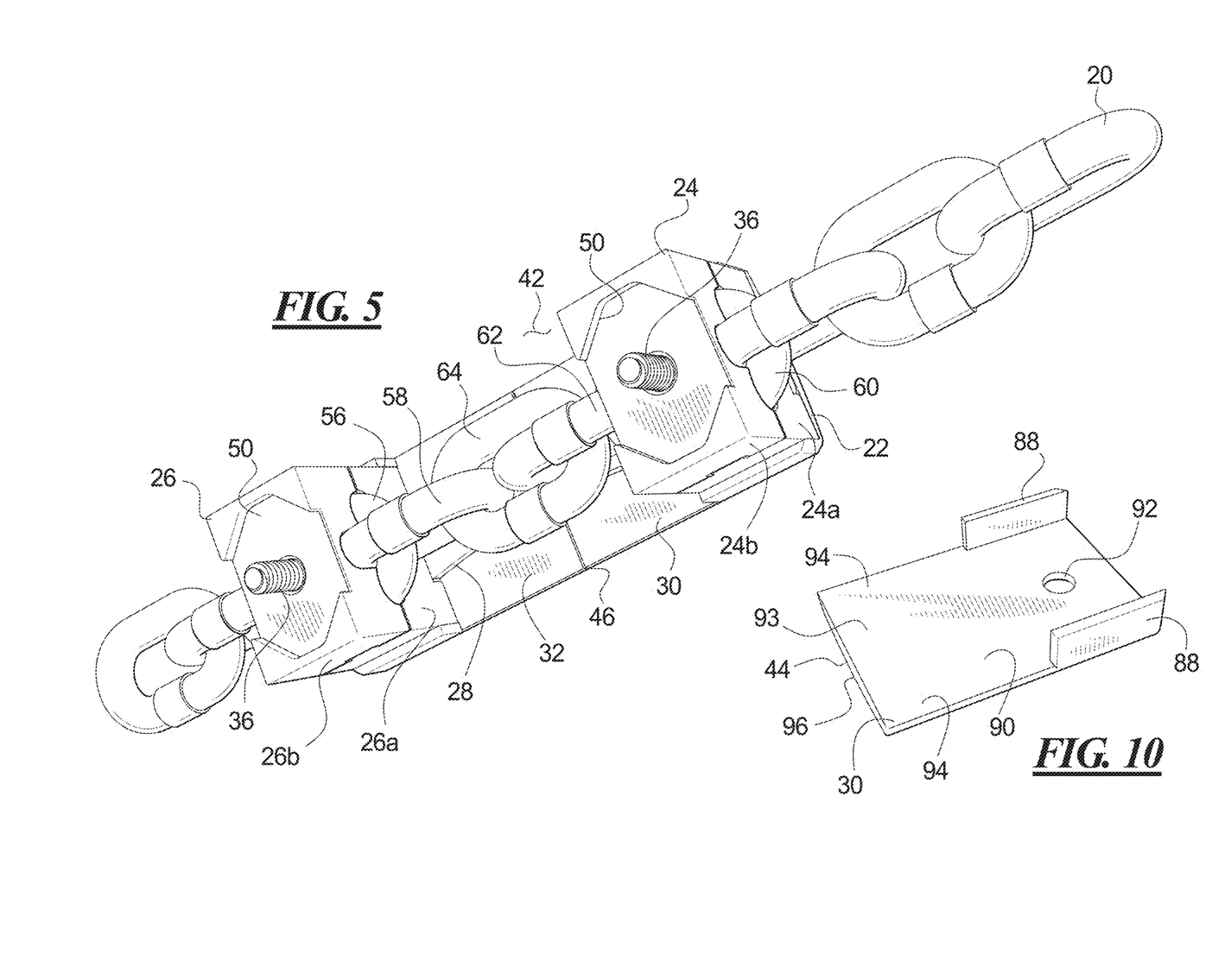
FIG. 5 is a side perspective view of the overload indicator with an indicator band removed to show the chain link mounting blocks.
FIG. 10 is a perspective view of a first portion of the side cover.

In FIG. 5, the first and second block portions 24 and 26 include the shaped recesses 50 into which the shaped portions of the indicator band 28 fits. As noted above, the shaped recesses 50 are generally hexagonal in shape to match the shape of the shaped portions 48. The bolts 36 extend through the block portions 24 and 26 and into the shaped recesses 50. The recesses 50 may have a depth corresponding to the thickness of the indicator band 28. The covers 30 and 32 may mount on to the overload indicator 22 and may press against the indicator band 28 or the block portions 24 and 26 or may press against both the indicator band 28 and the block portions 24 and 26 as a result of the recess 50 corresponding to the thickness of the indicator band 28.

The block portions 24 and 26 hold links of the chain 20 securely so that the lifting force of the load is carried by the overload indicator 22 without the block portions 24 and 26 slipping on the chain 20. The block portions 24 and 26 maintain a portion of the chain between the blocks in a slack condition. In the view of FIG. 5, a chain link 56 is mostly within the block portion 26 and a next chain link 58 extends from the block portion 26 into the gap 42. The link 58 may be held in a supported by the block 26 to maintain a position extending into the gap 42. Similarly, a chain link 60 is mostly in the block portion 24 and a next chain link 62 extends from the block portion 24 into the gap 42. The link 62 may be supported to maintain a position in the gap 42. A chain link 64, for example a middle link, connects the links 58 and 62. The middle link 64 is slack; no tension is exerted on the link 64 because the next links 58 and 62 are held in a position closer to one another than the link length of the middle link 64. In other words, a gap is present between the middle link 64 and one or both of the next links 58 and 62. in this example, the middle link 64 may rattle around as the overload indicator 22 is moved, even when under load.

Figures 6, 7:
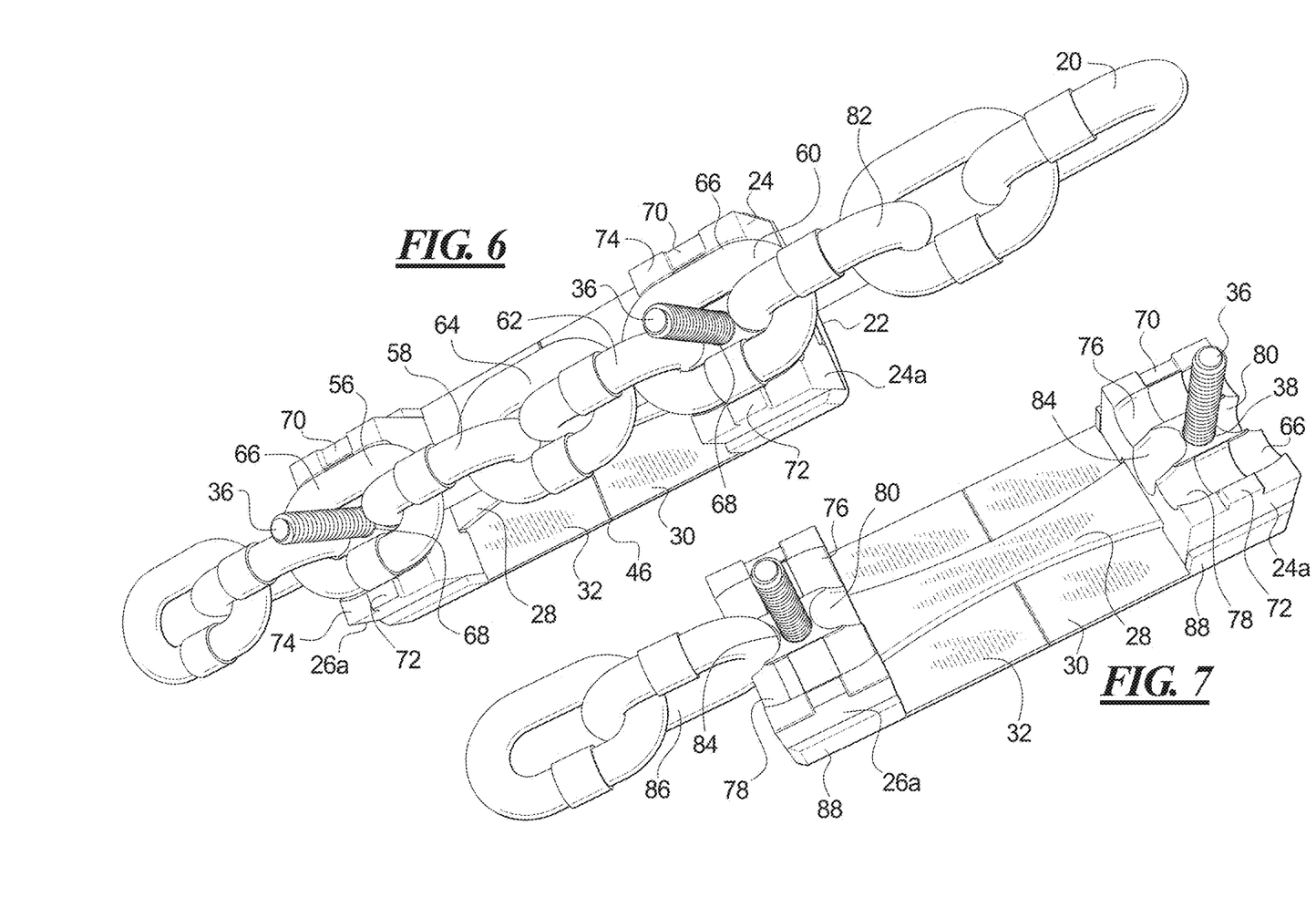
FIG. 6 is a side perspective view of the overload indicator with first portions of the chain link mounting blocks removed.
FIG. 7 is a side perspective view of the overload indicator with links of the chain removed to show the interior of the chain link mounting blocks.

FIG. 6 shows that the first and second block portions 24 and 26 are each formed in two parts, one part of which has been removed. In particular, the block portion 24 is formed of part 24a and part 24b. The part 24a is shown including a recess 66 to receive the chain link 60 and a bore 68 for receiving the bolt 36. An alignment recess 70 is provided on one side of the recess 66 and an alignment projection 72 is provided on the other side of the recess 66 extending into and out of, respectively, a connecting surface 74. The part 24b which has been removed for this view is similarly shaped with an alignment projection that extends into the alignment recess 70 and an alignment recess that receives the alignment projection 72. The parts 24b also has a chain recess like the recess 66 and a bore for the bolt 36.

In like manner, the second block portion 26 is formed of a first part 26a that has a chain recess 66, bore 68, an alignment recess 70, an alignment projection 72, and a connecting surface 74. The second part 26b which has been removed in this view has corresponding shapes.

FIG. 7 shows the first parts 24a and 26a including the chain recesses 66. The chain recess 66 of the illustrated example includes two parallel passages 76 and 78 into which the links 60 and 56 fit. A recess portion 80 receives a portion of a chain link 82 that is connected at one side of the link 60, and a recess portion 84 that receives the chain line 62 connected to the other side of the link 60. When the first part 24a is connected to the second part 24b with the chain held in the recesses 76, 78, 80 and 84, the chain 20 is prevented from slipping in the block portion 24. Similar recesses 76, 78, 80 and 84 are provided in the first part 26a of the second block portion 26. In the figure, a chain link 86 is shown in the recess 84 of the first part 26a. The chain link 86 is held in a position perpendicular with the link 56 that fits into the recesses 76 and 78 of the first part 26a.

In the view of FIG. 7, the second indicator band 28 is visible extend between the first and second block portions 24 and 26. The covers 30 and 32 are mounted adjacent the second indicator band 28 to cover the outside surface of the indicator band 28. The covers 30 and 32 include flanges 88 that extend on opposite sides of the block portions 24 and 26.

Figures 8, 9:
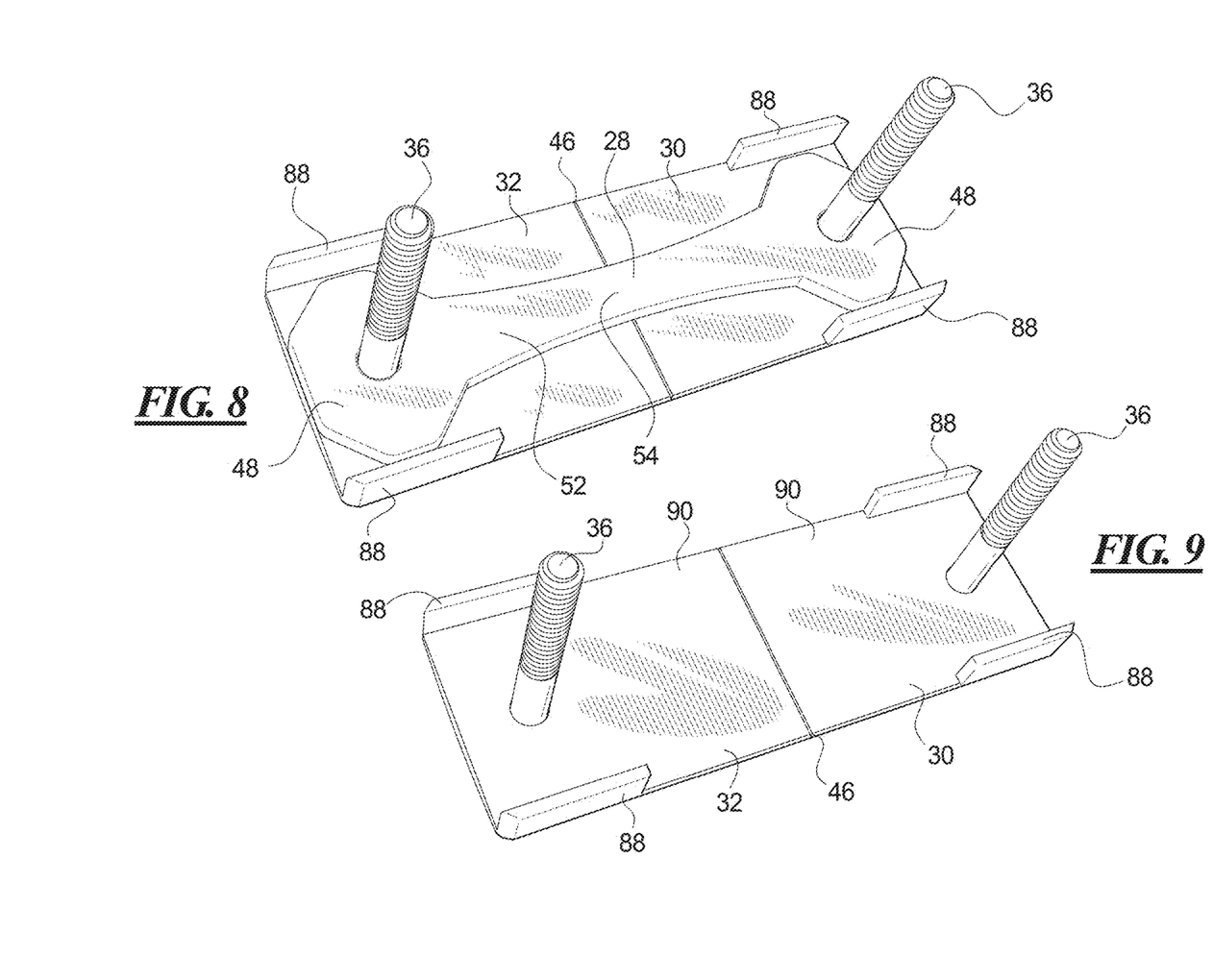
FIG. 8 is a top view of the overload indicator with the chain link mounting blocks removed to show an indicator band mounted to first and second side covers.
FIG. 9 is a top view of the overload indicator with the indicator band removed to show the first and second side covers and mounting bolts.

The block portions 24 and 26 have been removed in the view of FIG. 8. The indicator band 28 is connected between the bolts 36. The covers 30 and 32 are adjacent the indicator band 28. Each of the covers 30 and 32 include two flanges 88 that extend on opposite sides of the block portions 24 and 26.

In FIG. 9, removing the indicator band 28 shows the inner surfaces 90 of the covers 30 and 32. In the illustrated embodiment, the inner surfaces 90 are generally smooth. The indicator bands 28 that are adjacent to the covers may deform, stretch or otherwise be subjected to the threes on the overload indicator 22 without being effected by the covers 30 and 32.

FIG. 10 shows the cover 30 from the interior view. The cover 30 includes the interior surface 90 and the flanges 88. A bore 92 receives the bolt 36 which holds the cover 30 on the overload indicator 22. The cover 30 has the end 44 which is positioned against, near, adjacent or spaced from the end of the cover 32 to define the gap 42. The end 44 is shown as a generally planar surface, although surfaces of other shapes may be provided. The cross sectional shape of the cover 30 can be seen at the end 44. The cover 30 is thicker along a mid-line 93 and tapers to a thinner dimension toward the opposite edges 94 as a result of a curved outer surface 96. The interior surface 90 is flat in this example.

Figure 11:
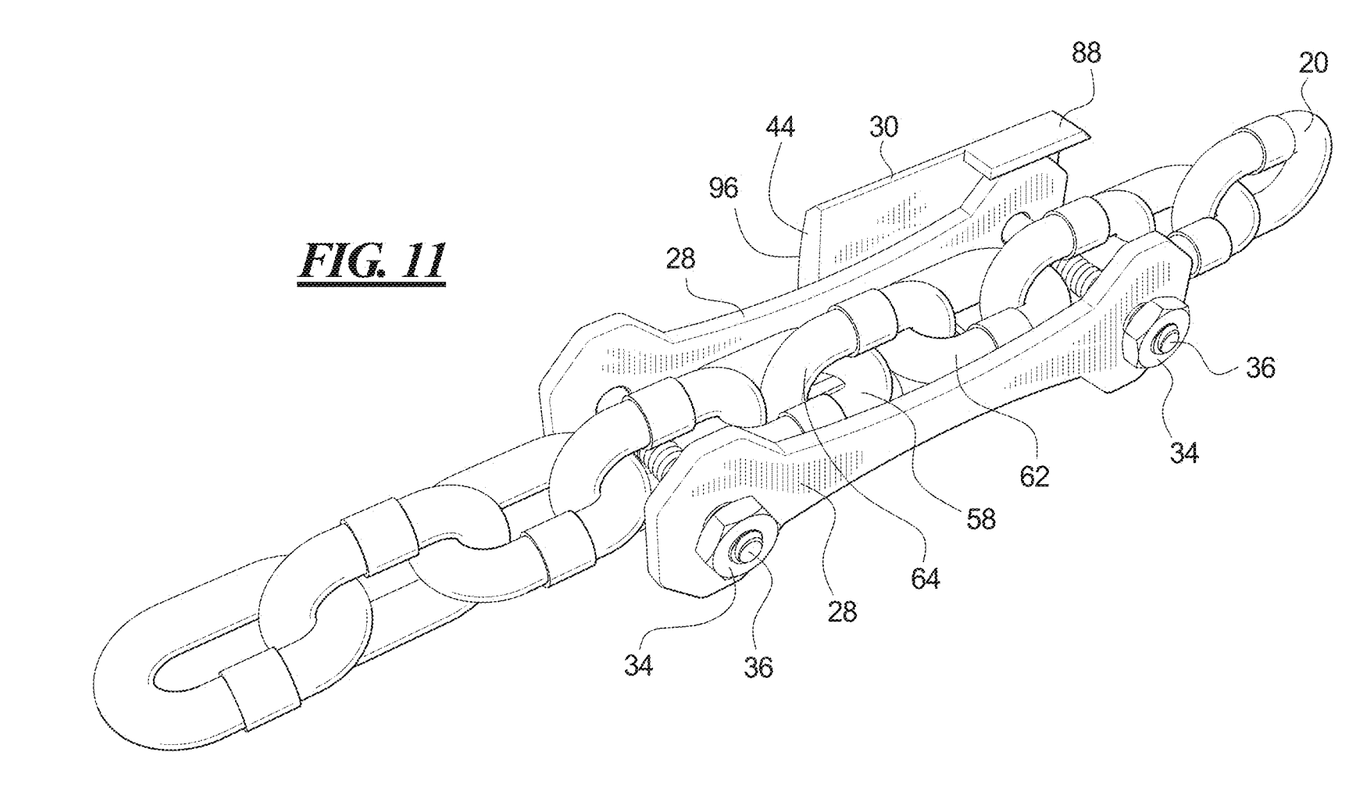
FIG. 11 is a side view of the indicator bands shown mounted in position on the chain, including a first portion of the cover.

With reference to FIG. 11, the chain 20 is held in a slack condition by the block portions 24 and 26 (not shown in this view) so that the middle chain link 64 is not under tension by the adjoining links 58 and 62. A gap can be seen between the link 64 and the adjoining link 58. The indicator bands 28 are disposed on two opposite sides of the chain 20 and generally are parallel to one another. The tension applied to the chain 20 that exceeds the deformation threshold of the indicator bands 28 will result in stretching or other deformation of one or both bands 28 up to the limit of the slack in the chain 20. If the indicator bands 28 stretch, break, or otherwise deform to the point that the slack is removed from the chain 20, then the chain 20 supports the load. This removes much of the load from the indicator bands 28, preventing further stretching of the indicator bands 28. The chain 20 functions as a safety for the overload indicator 22.

As the indicator bands 28 stretch, the distance between the bolts 36 increases. The cover 30 is connected to the bolt 36 and the other cover 32 is connected to the other bolt 36. Stretching of the indicator bands 28 increases the distance between the covers 30 and 32.

Figure 12:
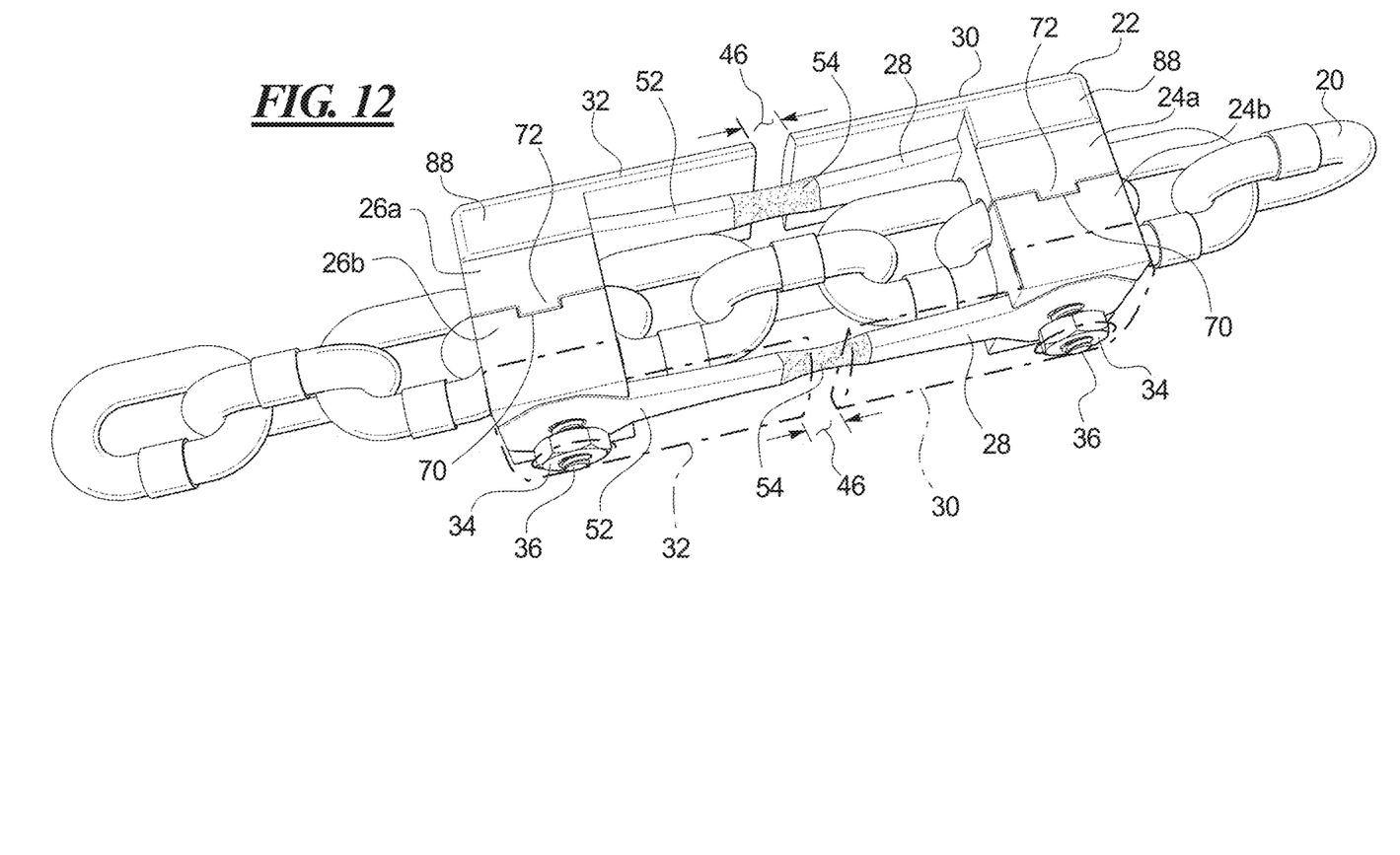
FIG. 12 is a side view of the overload indicator after the hoist has been used to lift a load over the threshold.

FIG. 12 shows the overload indicator 22 after the hoist has been used to lift a load greater than the threshold of the indicator bands 28. The indicator bands 28 have stretched as a result of the overload condition. The stretching of the bands 28 has moved the covers 30 and 32 apart, increasing the indicator gap 46. In one example, the indicator gap 46 has increased from a very small value with the surfaces 44 adjacent one another or touching to a noticeable gap length that may be easily seen by even casual inspection. The person viewing the overload indicator 22 is able to immediately determine that the hoist has been used to lift a load greater than the threshold. The hoist may be subject to a detailed inspection, may be repaired, or may be disposed of Failure of the hoist is avoided as well as possible damage to the hoist, the load, and/or damage or injury to surrounding persons or things, The indicator gap 46 has increased because the indicator bands 28 have stretched as a result of the overload. For example, the indicator bands 28 in the illustration have stretched at the weakened portion 54 in the tapered part 52. The stretching has narrowed the indicator bands 28 at the weakened portion 54, and in some cases may lead to breaking of the bands 28. The stretching may extend over some or all of the tapered part 52 or may be isolated to a small region.

The indicator bands 28 may be provided with paint or other coating. For example, a contrasting color paint or coating or material of the indicator bands 28 may be visible through the indicator gap 46. A brightly colored indicator band, for example of red, may be readily apparent to the viewer when the indicator gap has lengthened to permit a view of the indicator band 28. The paint or other coating may further indicate deformation or stretching of the indicator band 28. For example, as the material of the band 28 stretches, a non-stretchy paint will tend to crack, split, or otherwise leave gaps or openings that become apparent on inspection. The user may easily determine that the indicator band has stretched from cracks and gaps in the paint or other coating that are not present when the indicator band is un-stretched or un-deformed.

The readily apparent indication of an overload condition provided by the present overload indicator 22 may be used by a hoist operator to avoid damage to the hoist. If a load is being lifted by the hoist and the overload indicator 22 begins to show an overload condition, the hoist may be reversed to remove the load from the hoist. The hoist may remain undamaged as a result of the limited application of the overload.

The overload indicator 22 is less costly than the hoist so can be replaced at lower cost than the hoist on which it is mounted. The overload indicator 22 that has been deformed by lifting of an overload may be replaced in its entirety, or is may be possible to replace only the indicator bands 28. Damaged or deformed indicator bands 28 may be replaced by undamaged bands by merely removing the two bolts 36 and then re-assemblying the overload indicator with new bands. Other fasteners are of course possible The overload indicator 22 may be configured for different thresholds. For example, the overload indicator 22 may include indicator bands 28 that deform at one ton of applied weight. The overload indicator may be changed to indicate an overload condition of ½ ton, or 1.5 tons, or other value by exchanging the indicator band 28 for bands rated at the different threshold. The overload indicator 22 may be moved from hoist to hoist and configured to determine an overload condition for each hoist, even for hoists with different rated capacities. The indicator bands 28 may be marked with the threshold value or with a color or other indication of threshold value.

FIG. 13 shows an example of the present overload indicator in one application. A support 100 is provided. The support 100 may be a stationary or movable structure from which the hoist may be suspended to lift a load. A hoist 102 is connected to the support 100. The hoist 102 may be any type of hoist. In one example, the hoist 102 is an electrically powered hoist having a chain as the lifting medium. The chain 20 extends from the hoist 102. The overload indicator 22 is connected to the chain 20 as describe above so that a portion of the chain is held slack. A further portion of the chain 20 extends from the overload indicator 22. A load 104 is connected to the chain 20 portion that extends from the overload indicator 22. The chain 20 may be provided with a hook, rigging, sling or other connector element by which the load 104 is connected for lifting, holding and/or lowering by the hoist. Other means for connecting the load 104 may be provided instead.

Operation of the hoist 102 to apply tension to the chain 20 and lift the load 104 also applies the full force of the load 104 to the overload indicator 22. By providing the overload indicator 22 with indicator bands 28 that are configured to deform at a threshold, the indicator may indicate that the hoist 102 has been used to lift 104 a load greater than the threshold.

The indicator bands may be painted prior to being provided in the overload indicator. As stretching of the indicator bands occur, the paint on the surface of the indicator bands fragments, splits and/or separates to show an inspector that the band has been subject to an overload condition.

It is foreseen that the overload indicator may be used without the covers so that the indicator bands are directly visible to an inspector. The inspector may measure a length of the indicator bands, for example, or may examine a width or thickness of the weakened portion of the band, or may inspect paint on the band or other indication to determine whether the band has been deformed by an overload condition.

A plurality of indicator bands may be available for different thresholds of deforming or stretching values. The provider of the overload indicator may select from among the plurality of different value bands to obtain the indicator band having a desired value. The provider may insert the desired band for each different overload indicator, thereby matching the overload indicator threshold to the hoist on which it will be used.

The user may exchange indicator bands for different values, for example when transferring the overload indicator to a different hoist. If the overload indicator is mounted on a ½ ton hoist and it is desired to use the overload indicator on a 1 ton hoist, for example, the indicator bands may be exchanged for indicator bands of a different threshold so that the overload indicator may be used on the other hoist.

If the overload indicator has been used to lift a load greater than the threshold, resulting in the indicator bands being deformed, the indicator bands can be replaced with un-deformed indicator bands. Preferably the replacement of the indicator bands would occur in conjunction with inspection and/or repair of the hoist. The replacement of the indicator bands is performed by releasing the fasteners (the threaded nut and bolt fasteners of the illustrated embodiment), removing the covers and removing the indicator bands. New or other indicator bands are inserted in the place of the stretched or deformed indicator bands, the covers are replaced, and the fasteners secured to connect the components to one another.

It is foreseen that an additional indicator, for example an automatic indicator, may be provided in association with the overload indicator to indicate an overload condition. For example, an electronic, physical, visual or other sensor may be utilized to indicate stretching of the indicator band, separation of the covers, lengthening of the gap, or other changes indicating an overload condition. An output of the sensor may be used to take an action, such as provide an audible alarm, a visual indicator such as a light, or to act on the hoist, such as to halt hoist operation, Other actions are also possible.

The provider of the overload indicator or a user or other person may attach the overload indicator to a lifting medium such as a chain by attaching the parts of the blocks to the chain at spaced locations, attaching the indicator bands to the blocks, and attaching the covers to the blocks and bands, not necessarily in that order. The components may be fastened together, for example by the threaded nut and bolt as shown or by other fasteners. The attaching of the blocks to the chain may be performed by positioning a link of the chain in a recess of a part of the blocks, attaching the other part of the blocks to the first part of the blocks to capture the chain links, and fastening the overload indicator together with the fasteners.

It is foreseen that the overload indicator may be used on a wire cable or fiber rope lifting medium or other lifting medium by connecting the block portions to the lifting medium to provide a slack portion of the lifting medium. The overload indicator may be used in to indicate an overload condition that need not be the result of use of a hoist. For example, a crane or other lifting, carrying or holding device may be provided with the overload indicator.

The overload indicator includes two indicator bands positioned generally parallel to one another with the slack portion of the lifting medium between the indicator bands. Other arrangements are also possible, including a single indicator band, or three or more indicator bands. Multiple indicator bands may be mounted together on the overload indicator to provide multiples of the threshold. For example, a one ton hoist may be provided with two indicator bands that each deform at ½ ton. A two ton hoist may be provided with four ½ ton indicator bands. The bands may be formed to connected permit multiple bands to be mounted adjacent one another.

Although other modifications and changes may be suggested by those skilled in the art, it is the intention of the inventors to embody within the patent warranted hereon all changes and modifications as reasonably and properly come within the scope of their contribution to the art.

We claim:

1. An overload indicator for a hoist, the hoist having a lifting medium for lifting a load, comprising:
   first and second block portions connected to the lifting medium as spaced locations from one another, the spaced locations being such that the lifting medium is in a slack condition between the first and second block portions when the overload indicator is in a non-indicating position;
   an indicator band connected between the first and second block portions, the indicator band supporting substantially all of the load applied to the lifting medium when the overload indicator is in the non-indicating position, the indicator band being configured to at least one of stretch and deform and break upon application of a load greater than a predetermined threshold.

2. An overload indicator as claimed in claim 1, wherein the indicator band is a first indicator band and further comprising a second indicator band disposed approximately parallel with the first indicator band.

3. An overload indicator as claimed in claim 2, wherein the first and second indicator bands are disposed on opposite sides of the lifting medium with the slack portion of the lifting medium between the first and second indicator bands.

4. An overload indicator as claimed in claim 1, further comprising:
 first and second covers connected to the opposite ends of the indicator band.

5. An overload indicator as claimed in claim 4, wherein the first and second covers define an indicator gap between the first and second covers.

6. An overload indicator as claimed in claim 5, wherein the first and second covers are adjacent the indicator band on a first side of the lifting medium, and further comprising:
 a second side indicator band and second side first and second covers on a second side of the lifting medium, the first side and second side indicator bands and covers being parallel to one another.

7. An overload indicator as claimed in claim 1, further comprising:
 a first bolt extending through the first block portion and through a first end of each of the first and second indicator bands and through first portions of the cover; and
 a second bolt extending through the second block portion and through a second end of each of the first and second indicator bands and through second portions of the cover.

8. An overload indicator as claimed in claim 1, wherein the lifting medium includes a chain; and wherein the first and second block portions include shaped recesses to enclose portions of chain links of the chain.

9. An overload indicator as claimed in claim 1, wherein the first and second block portions each include first and second mating parts that are shaped to engage a portion of the lifting medium.

10. An overload indicator as claimed in claim 9, wherein the first and second mating parts are substantially identical to one another.

11. An overload indicator as claimed in claim 9, wherein the first and second mating parts each include a mating surface for engaging the other of the first and second mating parts, the mating surface including a projection and a recess, the projection of the first mating part fitting into the recess of the second mating part and the projection of the second mating part fitting into the recess of the first mating part when the first and second mating parts are engaged to the lifting medium.

12. An overload indicator as claimed in claim 1, wherein the first and second block portions each include a shaped recess, and wherein the indicator band includes first and second shaped ends configured to fit into the shaped recesses in respective ones of the first and second block portions.

13. A method for indicating that an overload condition has been applied to a hoist, comprising:
 attaching first and second blocks to a lifting medium of the hoist at first and second locations spaced from one another with a length of the lifting medium between the first and second blocks;
 attaching first and second indicator bands to the first and second blocks, the first and second indicator bands being generally parallel to one another and generally parallel to the length of the lifting medium between the first and second blocks, the indicator bands being configured to stretch or deform when subjected to a tension over a predetermined threshold;
 attaching covers over the indicator bands, the covers defining an indicator gap, wherein the indicator gap is a first gap distance when the indicator bands are in their un-stretched or un-deformed state and the indicator gap is at a second gap distance after the overload indicator has been used to lift a load greater than the predetermined threshold.

14. A method as claimed in claim 13, wherein the lifting medium is a chain, and
 wherein the attaching of the first and second blocks to the lifting medium includes:
 connecting a first part of the first block to a second part of the first block with a first portion of the chain between the first and second parts of the first block, and
 connecting a first part of the second block to a second part of the first block with a second portion of the chain between the first and second parts of the second block.

15. A method as claimed in claim 14, further comprising:
 fastening the first and second parts of the first block and the indicator bands and first portions of the covers together with a first fastener; and
 fastening the first and second parts of the second block and the indicator bands and second portions of the covers together with a second fastener.

16. A method as claimed in claim 13, wherein the first and second indicator bands are indicator bands of a first threshold, and further comprising:
 exchanging the indicator bands of the first threshold for indicator bands of a second threshold in the overload indicator.

17. A method as claimed in claim 13, further comprising:
 selecting the first and second indicator bands from a plurality of indicator bands having a plurality of different thresholds.

* * * * *